United States Patent [19]

Garth et al.

[11] Patent Number: 4,643,719
[45] Date of Patent: Feb. 17, 1987

[54] MANUALLY OPERABLE ASPIRATOR

[76] Inventors: Geoffrey C. Garth, 334 Colorado Pl., Long Beach, Calif. 90814; Charles A. Patterson, 314 C Monte Vista, Costa Mesa, Calif. 92627

[21] Appl. No.: 632,306

[22] Filed: Jul. 19, 1984

[51] Int. Cl.$^4$ ............................................. A61M 1/06
[52] U.S. Cl. ..................................... 604/73; 604/133; 604/315
[58] Field of Search ............... 128/205.18; 604/73, 604/131, 133, 134, 327, 328, 247, 74, 313–316; 417/472, 473, 566; 137/844; 251/319; 433/95

[56] References Cited

U.S. PATENT DOCUMENTS

| | | | |
|---|---|---|---|
| 862,867 | 8/1907 | Eggleston | 417/390 |
| 2,421,679 | 6/1947 | Bingham, Jr. | 417/472 |
| 2,428,451 | 10/1947 | Emerson | 128/205.18 |
| 2,688,979 | 9/1954 | Kendrick | 3/1.5 |
| 2,947,470 | 8/1960 | Ruben et al. | 230/160 |
| 3,084,691 | 4/1963 | Stoner | 128/278 |
| 3,376,868 | 4/1968 | Mondiadis | 128/278 |
| 3,387,610 | 6/1968 | Richmond | 128/278 |
| 3,421,504 | 1/1969 | Gibsons | 128/278 |
| 3,454,007 | 7/1969 | Salis | 128/232 |
| 3,742,952 | 7/1973 | Magers et al. | 128/278 |
| 3,774,611 | 11/1973 | Tussey et al. | 128/278 |
| 3,779,243 | 12/1973 | Tussey et al. | 128/278 |
| 3,782,385 | 1/1974 | Loyd | 128/281 |
| 3,875,941 | 4/1975 | Adair | 604/133 |
| 3,886,937 | 6/1975 | Bobo et al. | 137/843 |
| 3,938,514 | 2/1976 | Boucher | 128/232 |
| 3,939,830 | 2/1976 | da Costa | 128/205.18 |
| 4,068,662 | 1/1978 | Sneider | 128/232 |
| 4,539,985 | 9/1985 | Magrath | 604/133 |

FOREIGN PATENT DOCUMENTS

| | | | |
|---|---|---|---|
| 351236 | 4/1920 | Fed. Rep. of Germany | 604/73 |
| 854397 | 8/1981 | U.S.S.R. | 604/316 |

OTHER PUBLICATIONS

Medical Instrumentation Publication.

Primary Examiner—C. Fred Rosenbaum
Assistant Examiner—J. L. Kruter
Attorney, Agent, or Firm—Fulwider, Patton, Rieber, Lee & Utecht

[57] ABSTRACT

An aspirator for removing vomit and like matter from the mouth and throat. A bellows integral with a collection reservoir includes a handle grip reciprocable alternately to draw vomit into the reservoir from an attached catheter insertable into the throat, and vent air through an exhaust valve. The bellows-reservoir unit is detachably mounted to a frame which also includes a handle grip and springs. The grips are squeezed to draw in vomit, and released to permit the springs to collapse the bellows. The operation is one-handed, the device is portable, and the bellows-reservoir unit can be separated from the frame and discarded after use. A feature is a one-way inlet valve in the catheter to prevent vomit from draining back into the throat during aspirator operation.

9 Claims, 14 Drawing Figures

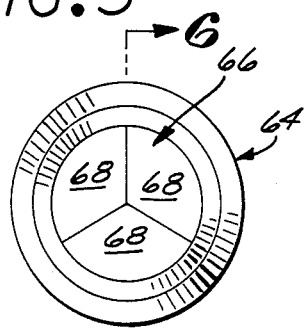
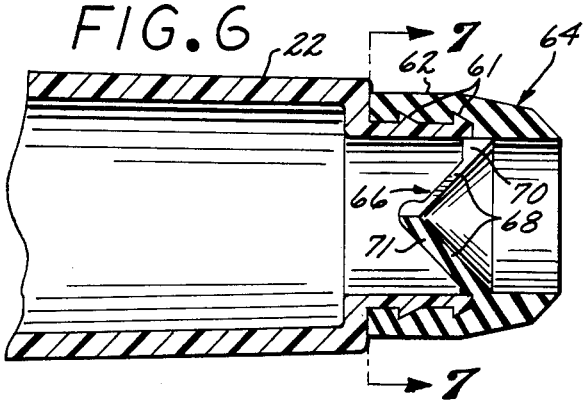
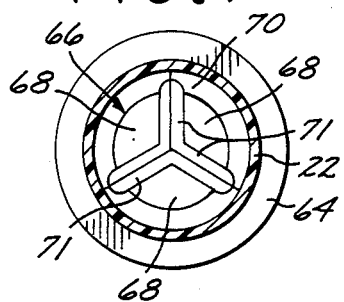
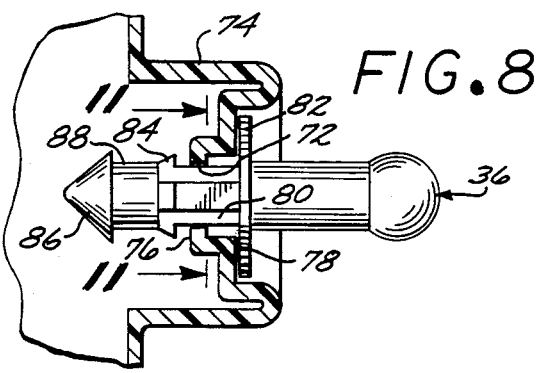
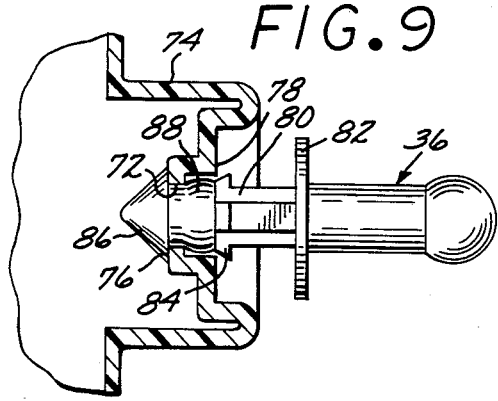
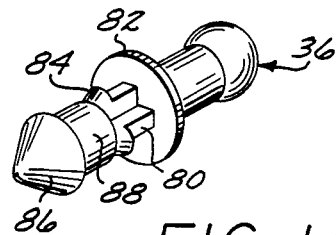
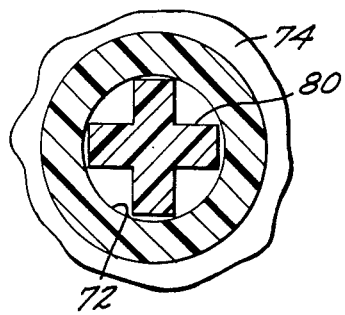
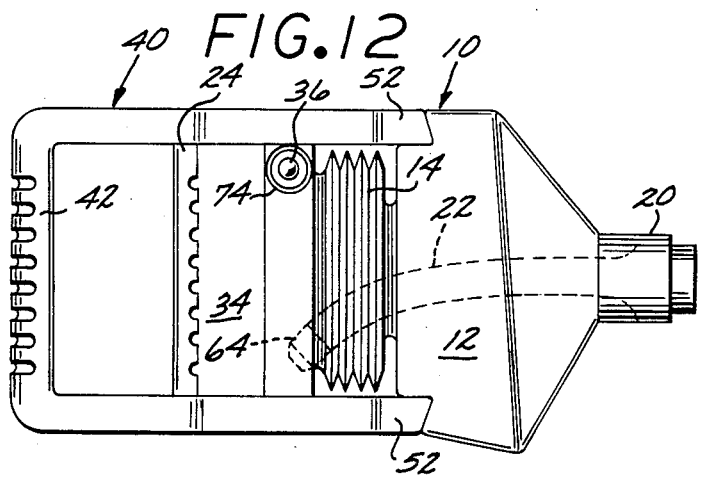

MANUALLY OPERABLE ASPIRATOR

BACKGROUND OF THE INVENTION

1. Field of the Invention

The present invention relates to portable hand operable aspirators for removing matter from a body cavity, and particularly vomit and like matter from the mouth and throat.

2. Description of the Prior Art

Continuous suction aspirators for use in removing fluid and the like from body cavities are well known. Such aspirators are typically found in hospitals, where their operation can be monitored by hospital personnel. Loss of suction or vacuum is not a problem because of continuous operation of the associated motor operated vacuum pump.

The siphon tube or catheter of such an aspirator is relatively small in diameter because of the nature of the fluids extracted from body cavities and wounds. However, where the aspirator is used to remove matter such as vomit from the throat, the catheter is subject to clogging. Fortunately, the presence of monitoring personnel, as needed, permits immediate attention to the problem of clearing the catheter. It is critical that vomit, for example, not be allowed to drain back into the patient's throat because it could then be drawn into the lungs and present the severe danger of virulent infection. Such reverse flow is not possible if the vacuum pump is operated continuously to provide a steady vacuum.

The weight, complexity and expense of motor operated hospital type aspirators limit their use in emergency situations by ambulance personnel and paramedics. In addition, there is usually no ready source of power for their operation, aside from batteries with their obvious shortcomings.

A few portable, hand or foot operated aspirators have been proposed for use by emergency personnel, but they have been found to be largely impractical for a variety of reasons. Some require the use of both hands, and one hand is usually needed to guide the catheter into the patient's throat. Some are difficult to sterilize for reuse. Most are subject to clogging, particularly where in-line filters are used. The dilemma posed is that when the catheter is made large enough to easily pass vomit, there is the potential for back-flow of this matter into the throat and lungs of the victim.

SUMMARY OF THE INVENTION

According to the present invention, a portable, hand operable aspirator is provided which, in one embodiment, includes a collection means detachably connected to a frame so that the collection means can be separated and thrown away after a single use. Opposed handles on the collection means and frame are adapted to be repeatedly squeezed and released with one hand to operate the device. One handle is integral with the frame and the other handle is integral with a bellows which, in turn is integral with a reservoir, the bellows and reservoir comprising the collection means, which also includes an inlet and an exhaust or vent valve. A siphon tube or catheter is mounted to the collection means adjacent the inlet so that vomit is drawn into the reservoir upon squeezing of the handles and consequent expansion of the bellows. The catheter is of relatively large diameter to prevent clogging by vomit material. Bias means carried by the frame act to separate the handles upon their release to collapse the bellows and vent air through the exhaust valve.

With the exhaust valve open there is negligible differential pressure across the catheter, but typically there exists a column of vomit in the catheter. A unique self-closing one-way inlet valve means is located between the distal extremity of the catheter and the collection means, preferably adjacent the distal extremity. This valve automatically closes to prevent undesirable reverse flow, which would very likely otherwise occur because of the desired relatively large diameter of the catheter.

Other objects and features of the invention will become apparent from consideration of the following description taken in connection with the accompanying drawings.

BRIEF DESCRIPTION OF THE DRAWINGS

FIG. 5 is an enlarged view taken along the line 5—5 of FIG. 1

FIG. 6 is a view taken along the line 6—6 of FIG. 5;

FIG. 7 is a view taken along the line 7—7 of FIG. 6;

FIG. 8 is an enlarged view taken along the line 8—8 of FIG. 2, illustrating the exhaust valve in its inwardly disposed, operative position;

FIG. 9 is a view similar to FIG. 8, but illustrating the exhaust valve in its outwardly disposed, sealed position preparatory to discarding of the associated collection means;

FIG. 10 is a perspective view of the exhaust valve of FIGS. 8 and 9;

FIG. 11 is a view taken along the line 11—11 of FIG. 8;

FIG. 12 is a view similar to FIG. 1, but illustrating the inwardly disposed, protected position of the catheter prior to use;

DESCRIPTION OF THE PREFERRED EMBODIMENT

Figure 1:
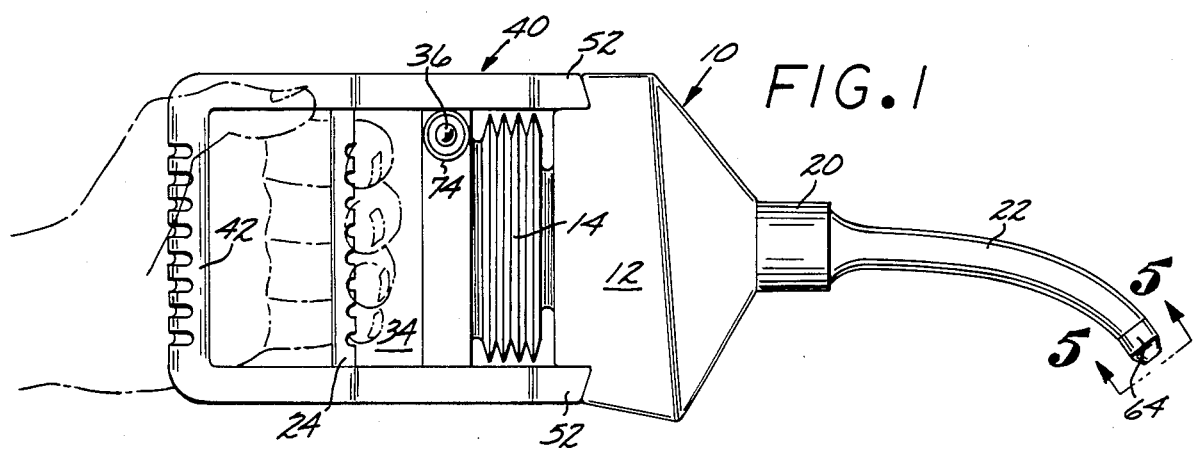
FIG. 1 is a side elevational view of an aspirator according to the present invention, the manner of single-handed operation being shown in phantom outline.

Referring now to the drawings, an aspirator is illustrated which comprises, generally, a relatively thin wall collection means 10 preferably molded of inexpensive polyethylene material or the like, having a hollow reservoir 12 in fluid communication with a movable vacuum control portion or accordion bellows 14 which is integral with the reservoir 12.

The reservoir 12 is characterized by an opening or inlet 16 defined by a protruding boss 18 having external screw threads for threadably mounting an internally threaded syringe sleeve 20.

Figure 3:
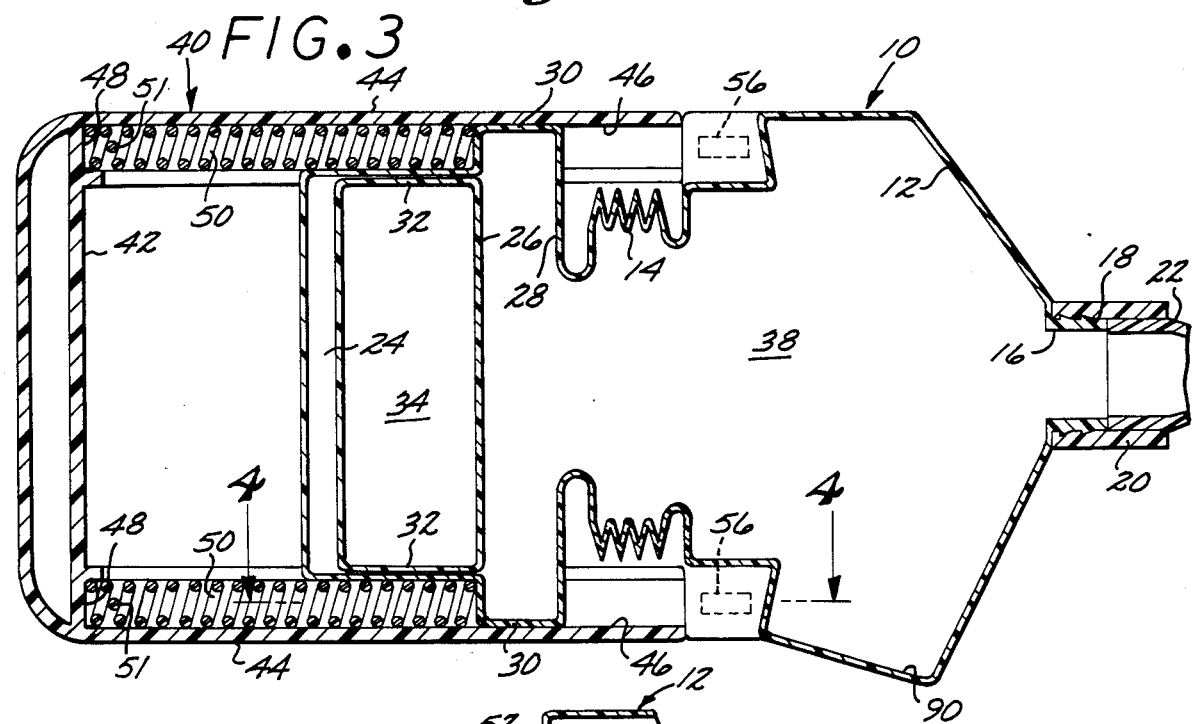
FIG. 3 is an enlarged view taken along the line 3—3 of FIG. 2.

The inner or proximal extremity of a siphon tube or catheter 22 is removably frictionally received within the sleeve 20 in abutment with the boss 18. The projecting orientation of the catheter 22 illustrated in FIGS. 1 and 3 is the operative position of the catheter 22. However, the proximal extremity of the catheter 22 may be withdrawn and the catheter reversed in position so that the distal extremity projects into the interior of the reservoir 12, as best illustrated in FIG. 12. This makes the assembly more compact for shipping and also protects the catheter 22 from contamination, particularly when the assembly is encompassed within a protective wrapping or blister pack (not shown), as will be apparent to those skilled the art.

The catheter 22 is characterized by a relatively large diameter curvature to facilitate its insertion into the throat of a patient or accident victim. The inner diameter of the catheter 22 is relatively large, in the order of ½ inch, as compared to a more typical inner diameter of ⅛ to ¼ of an inch which characterizes hospital-type catheters. The relatively large diameter is adapted to freely pass vomit toward the inlet 16.

Figure 4:
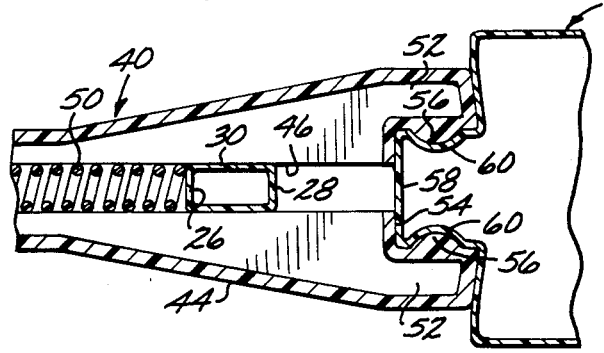
FIG. 4 is a detail view taken along the line 4—4 of FIG. 3.

The accordion portion of the bellows 14 has a diameter less than the transverse cross-section of the adjacent portion of the reservoir 12, while the inward or rear portion of the bellows 14 comprises a handle guide structure defined by longitudinally spaced apart wall portions 26 and 28 which are configured to form upwardly and downwardly directed abutments 30, as best seen in FIGS. 3 and 4.

The bellows 14 also includes a hollow bellows handle 24 spaced rearwardly of the wall 26 by hollow longitudinally directed handle supports 32 integral with the wall 26. The hollow portions of the handle 24 and supports 32 provide overflow chambers in fluid communication with the interior 38 defined by the reservoir 12 and bellows 14.

The spacing of the handle 24 from the wall 26 defines a finger opening 34 for the operator's fingers, as shown in phantom outline in FIG. 1. Inward movement of the bellows handle 24 is operative to compress the accordion portion of the bellows 14 and thereby decrease the volume of the interior 38, the air being vented from the interior 38 through a vent or exhaust valve 36 which is a part of the collection means 10. Conversely, upon outward movement of the handle 24, the volume of the interior 38 is increased, closing the exhaust valve 36, and reducing the pressure in the interior 38 for siphoning of material through the catheter 22 and into the interior 38. As evident in FIG. 1, the exhaust valve 36 is located for communication with the upper, rearward portion of the interior 38 so that such material cannot escape out of the interior 38 until it is filled to near capacity.

It is possible for the bellows handle 24 to be reciprocated in a two-handed operation, with one hand holding the reservoir 12 and the other gripping the handle, but preferably the aspirator includes a frame 40 to enable one-handed operation of the aspirator. The frame is preferably made of any plastic material suitable for injection molding and durable enough for more than one use.

Figure 2:
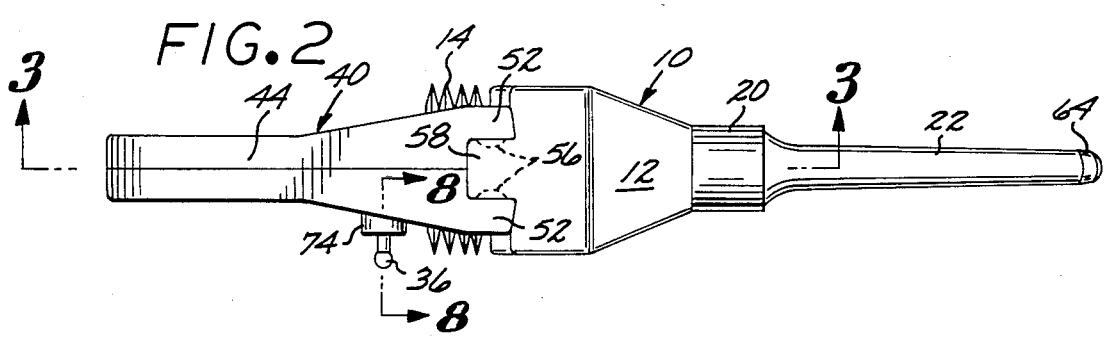
FIG. 2 is a top plan view of the aspirator of FIG. 1.

As best seen in FIG. 2, the frame is characterized by opposite halves which are adhered together to define a transversely oriented frame handle 42 adjacent the bellows handle 24 and adapted to support the hand of the user so that the operator can reciprocate the handle 24 by alternately squeezing and releasing the handle 24. The frame 40 includes longitudinally directed upper and lower portions 44 which are configured to define tracks or channels 46 which longitudinally slidably receive the handle abutments 30. The rearward extremities of the channels 46 terminate in integral stop walls 48 which are engaged, respectively, by the rearward extremities of a pair of bias means or compression springs 50. The springs extend through the channels 46 and engage the handle abutments 30 at their forward extremities, and are operative to bias the handle 24 inwardly to compress the bellows 14 on operator release of the handle 24. The springs 50 are captured or held within the channels 46 by posts 51 which are integral with the opposite halves of the frame, and which protrude between end ones of the coils of the springs 50 when the halves are assembled and adhered together. With this arrangement the springs 50 are held within the channels 46 when, as will be seen, the collections means 10 is demounted from the frame 40 after use.

The frame portions 44 are transversely enlarged at their forward extremities to provide bifurcations or mounting yokes 52 which are spaced apart to define a mounting recess 54 characterized by laterally opposed arcuate shaped detents 56.

The upper and lower rearward extremities of the wall defining the reservoir 12 form a rearwardly directed mounting plug 58 characterized by laterally inwardly directed arcuate grooves or mounting seats 60 adapted to closely receive the detents 56. By virtue of the material of the reservoir 12 and its modest wall thickness, the plug 58 is adapted to deflect sufficiently to enable the seats 60 to be forcibly pushed onto the detents 56 in a snap-in action. With this arrangement, the collection means 10 can be disposed after one use simply by forcibly pulling upon the collection means 10 to separate it from the frame 40 upon disengagement of the detents 56 from the seats 60. A fresh or replacement collection means 10 is quickly mountable to the frame 40 by reversing this procedure, as will be apparent.

Referring particularly to FIGS. 5-7, the distal extremity of the elongated catheter 22 includes a reduced diameter portion which includes circumferential ridges adapted to forcibly fit or snap within complemental circumferential recesses provided in a cylindrical skirt 62 of a one-way inlet valve 64. The valve 64 is made of elastomeric material such as rubber and preferably is also adhesively secured to the skirt 62 to insure against inadvertent separation of the valve 64 from the skirt 62. As evident from the drawings, the interior 38 is closed to atmosphere except for the valve 64 and the exhaust valve 36.

The valve 64 is generally cylindrical and includes a generally transversely oriented inner wall 66 divided or cut into a plurality of valve petals 68 disposed inwardly and centrally from the base 70 of the wall 66 to an axially centrally located apex, as seen in FIGS. 5 through 7. Preferably three petals 68 are provided. In their closed position the petal side margins abut and their tips meet at the apex or central portion of the inner wall 66 whereby vomit is constrained against reverse flow or outward movement past the wall 66.

Although not illustrated, in their open position the valve petals 68 are pivoted about their bases 70 to generally axially directed positions which provide a large opening for inward passage of vomit. The elastomeric material of the valve 64 causes the valve petals 68 to move from their open positions defining a passage means into the catheter 22, to their closed positions in the absence of differential pressure across the valve 64. As best seen in FIGS. 1-3, the inlet 16 at one end of the catheter 22 and the valve 64 at the other end of the catheter constitute the only openings to the catheter.

As best seen in FIG. 7, the adjacent margins of the valve petals 68 are characterized by thickened portions 72 for better sealing and leakage prevention, the thicker side margins constraining the valve petals 68 to abut rather than overlap.

The projecting skirt 62 of the valve 64 serves a dual function. Its soft elastomeric character prevents injury or irritation of the sensitive tissue of the throat lining by compressing on initial contact. In addition, the presence of the skirt 62 acts as a buffer to protect the valve petals 68 from being squeezed and deformed through contact with the throat, and adversely affecting their operation. It is virtually impossible to deform the valve petals 68 by pushing the skirt 62 against a surface such as the throat because the petals 68 are peripherally supported against this by the relatively rigid reduced diameter portions of the distal extremity of the catheter 22.

Figure 13:
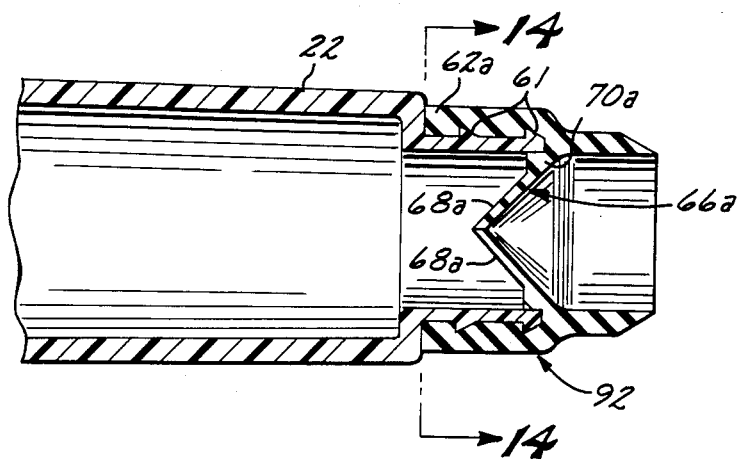
FIG. 13 is a view similar to FIG. 6, but illustrating another form of inlet valve.
Figure 14:
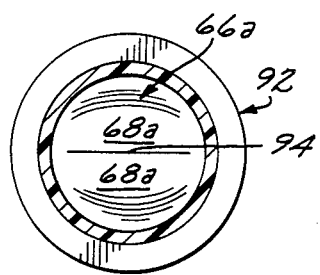
FIG. 14 is a view taken along the line 14—14 of FIG. 13.

A modified form of one-way valve 92 is illustrated in FIGS. 13 and 14. Certain component parts of valve 92 have virtually identical counterparts in valve 64, and these components are identified with similar numerals, with the subscript "a" employed for the valve 92 component parts.

Valve 92 includes an inner wall 66a which, instead of being divided into the three valve petals 68 of the valve 64, is formed into a "duck-bill" configuration. From the circular base 70a, the wall 66a extends radially and axially inwardly to define a cone having an apex 94. The apex 94 is the center of a cut or slit 96 which divides the wall 66a into two valve petals, flaps or portions 68a.

The resilient, soft material of valve 92 allows the portions 68a to separate at their tips or margins at a typical partial vacuum or internal negative pressure of 12 inches of mercury, for example, and pass particles of up to ⅜ inches across. Conversely, the resilience of the valve material causes the portions 68a to come together, closing the slit 96, when internal negative pressures drop to 0 to 6 inches of mercury. The closure is complete at no back pressure so that there is no leakage during release of the handles 24 and 42. The two flap "duck-bill" configuration of valve 92 is simpler to fabricate than the configuration of valve 64, but it is believed that the valve 64 is characterized by a larger opening for particle flow for the same size interior wall 66/66a. Particle flow is also facilitated by the fact that the internal diameter of both valve 64 and valve 92 is not greater than the internal diameter of catheter 22, as is evident in FIGS. 6 and 13.

As best seen in FIGS. 8-11, the exhaust valve 36 is made of elastomeric material such as silicone rubber, and is received within a passageway or exhaust opening 72 formed in a transverse wall of a boss 74 integral with the portion of the bellows 14 defining the guide abutments 30. The wall includes an outer face 78, and is characterized by an inwardly directed, reduced diameter portion having an inner face 76 and an opening which constitutes the exhaust opening 72.

The exhaust valve includes an elongated body portion 80 which is cut away or formed of reduced cross-section to provide longitudinal vent passages through to the exhaust opening 72.

Adjacent opposite extremities of the narrow body portion 80, the exhaust valve 36 includes an outer sealing means or disk 82 and an intermediate stop 84 in the form of a plurality of radially outwardly directed quadrants engageable with the inner face 76 to limit outward movement of the valve 36 in the operative position illustrated in FIG. 8. In this position internal pressures acting upon the valve 36 move it outwardly and permit air to move past the narrow body portion 80 and around the unseated disk 82 to atmosphere. Conversely, reduced pressures seat the disk 82 against the outer face 78 and prevent ingress of air.

The exhaust valve 36 has another position, as seen in FIG. 9, in which it can be placed to completely plug or seal the collection means 10 to insure against leakage of the contents when the collection means 10 is to be forceably separated from the frame 40 and discarded. For this purpose, the exhaust valve inner extremity includes a concially shaped inner stop 86 adapted to seat against the inner face 76. In addition, the valve 36 includes a cylindrical inner seal 88 located between the stops 84 and 86 and adapted for receipt within the exhaust opening 72 to seal it off against any fluid leakage.

The diameter of the seal 88 is greater than the inner diameter of the exhaust opening 72 so that when the protruding outer extremity of the valve is manually grasped and pulled, the seal 88 is stretched and reduced in cross section. In addition, the intermediate stop 84 is deformed inwardly so that it can be forcibly pulled through the exhaust opening 72 to the position of FIG. 9, where it is seated against the outer face 78. When the protruding outer extremity is released, the inner seal 88 expands and completely fills the opening 72 to seal the interior of the collection means 10. Further outward movement of the valve 36 is prevented by engagement of the inner stop 86 with the inner face 76.

In operation, the distal extremity of the catheter 22 is guided into the throat of the accident victim, for example, and the other hand of the operator is used to reciprocate the handle 24 to repeatedly expand and collapse the bellows 14. On bellows expansion, the reduced pressure in the interior 38 draws vomit through the inlet valve 64, into the interior of the catheter 22, through the inlet 16, and initially into a depression 90 integrally formed in the reservoir 12, as seen in FIG. 3. As is apparent from the drawings, and particularly FIGS. 1 and 3, the exhaust valve 36 is located adjacent the upper rearward portion of the interior 38 whereby vomit cannot escape through the valve 36 until the interior 38 is filled with vomit to near capacity. Further, the exhaust valve 36 is located above the catheter 22, out of the path of flow of vomit coming into the interior 38, to prevent clogging of the exhaust valve 36.

On release of the handle 24, any quantity or column of vomit in the catheter 22 will be under negligible pressure from the interior 38 inasmuch as air is being vented from the interior 38 through the exhaust valve 36. The relatively generous internal dimensions of the catheter 22 typically will not prevent back flow or drainage of the vomit by capillary action. However, the resilience of the inlet valve 64 is such that the valve petals 68 automatically move to their closed position despite the lack of any differential pressure, and thereby prevent backflow of material into the throat.

Desirably, the inlet valve 64 is located in the distal extremity of the catheter 22. However, under certain circumstances it may be possible to locate the valve 64 at the opposite or proximal extremity, or even interiorly adjacent the inlet 16. This will depend upon the catheter diameter, length of the column and the like. Thus, if the top of the column is sealed, the material in the column will be retained unless the column is too long or the column diameter is too great.

Although not illustrated, the inlet valve 64 can be located in the distal extremity of the catheter 22, and an elongated open but smaller catheter extension (not shown) attached to the catheter 22. Such an extension enables the present aspirator to be used for small children and infants. The column length and diameter of the small extension would be effective to prevent reverse flow of vomit in that a catheter extension, even though the valve 64 would be located at the proximal rather than the distal extremity of the extension.

The present aspirator is thus easily portable, manually operable with one hand, and characterized by a collection portion made of such inexpensive materials that it can be discarded after a single use. Most importantly, however, the aspirator is characterized by a unique form of inlet valve adapted to prevent undesirable reverse flow of material drawn into the catheter, while yet providing a catheter of generous internal dimensions adequate to easily pass vomit and like matter.

Various modifications and changes may be made with regard to the foregoing detailed description without departing from the spirit of the invention.

I claim:

1. An aspirator for removing vomit and like matter from the mouth and throat, said aspirator comprising:
   collection means including a bias means and a substantially closed reservoir having a horizontally disposed longitudinal axis and an interior defining a proximal end and a distal end for receiving vomit, and further including a vacuum control portion manually reciprocable to decrease and increase, respectively, the volume of said interior, said vacuum control means being movable against the bias of said bias means to increase said volume, said collection means further including an inlet to said interior and a one-way exhaust valve located in the upper portion of said interior transversely displaced from said longitudinal axis and above said inlet, substantially adjacent said proximal end, whereby said exhaust valve is out of the path of vomit entering said interior through said inlet, and whereby vomit cannot pass out of said exhaust valve until said interior is filled to near capacity, said exhaust valve being operative to vent air to atmosphere from said interior upon said decrease of said volume, said exhaust valve being located on a wall of said reservoir, said interior being otherwise closed to atmosphere to prevent escape of collected vomit;
   an elongated catheter in communication at its proximal extremity with said inlet, the distal extremity of said catheter having an internal diameter sufficiently large to pass vomit freely toward said inlet upon said increase of said volume; and
   one-way valve means operative upon said increase of said volume to define passage means into said catheter in the immediate region of said distal extremity to pass vomit freely through said passage means and toward said inlet and operative upon said decrease of said volume to close said passage means and prevent vomit in said catheter from passing back into the throat, said inlet and said passage means constituting the only openings into said catheter, said inlet valve having an internal diameter no greater than said internal diameter of said catheter to facilitate passage of vomit through said catheter toward said inlet.

2. An aspirator according to claim 1 wherein said vacuum control portion comprises an accordion type bellows defining an internal space forming a part of said interior of said collection means.

3. An aspirator according to claim 1 wherein said vacuum control portion comprises an accordion type bellows located remote from said inlet, and the remainder of the interior of said collection means comprises a reservoir adjacent said inlet and adapted to collect vomit passing into said interior.

4. An aspirator for removing vomit and like matter from the mouth and throat, said aspirator comprising:
   collection means including a substantially closed reservoir having a horizontally disposed longitudinal axis and an interior defining a proximal end and a distal end for receiving vomit, and further including a vacuum control portion comprising an accordion type bellows and an integral movable handle movable to decrease and increase, respectively, the volume of said interior, and a one-way exhaust valve located in the upper portion of said interior transversely displaced from said longitudinal axis and above said inlet, substantially adjacent said proximal end, whereby said exhaust valve is out of the path of vomit entering said interior through said inlet, and whereby vomit cannot pass out of said exhaust valve until said interior is filled to near capacity, said exhaust valve being operative to vent air upon said decrease of said volume, said exhaust valve being located on a wall of said reservoir;
   an elongated catheter in communication at its proximal extremity with said inlet, the distal extremity of said catheter being adapted for insertion into the throat, said catheter having an internal diameter sufficiently large to pass vomit freely toward said inlet upon said increase of said volume;
   one-way inlet valve means operative upon said increase of said volume to define passage means into said catheter in the immediate region of said distal extremity to pass vomit freely through said passage means and toward said inlet, and operative upon said decrease of said internal volume to close said passage means and prevent vomit in said catheter from passing back into the throat; and
   a frame detachably connected to said collection means and defining a fixed handle member and guideways adjacent said fixed handle member, and further including elongated spring means in said guideways engaged by said movable handle member, said bellows and movable handle member being movable inwardly by said spring means and movable outwardly by grasping and squeezing together of said fixed and movable handle members by an operator.

5. An aspirator according to claim 4 wherein said collection means includes detents and said frame include projections detachably receivable in said detents whereby said collection means are forcibly separable from said frame.

6. An aspirator for removing vomit and like matter from the mouth and throat, said aspirator comprising:
   collection means including a bias means and a substantially closed reservoir having a horizontally disposed longitudinal axis and an interior defining a proximal end and a distal end for receiving vomit, and further including a vacuum control portion movable to decrease and increase, respectively, the volume of said interior, said vacuum control means being movable against the bias of said bias means to increase said volume, said collection means further including an inlet to said interior and a one-way exhaust valve located in the upper portion of said interior transversely displaced from said longitudinal axis and above said inlet, substantially adjacent said proximal end, whereby said exhaust valve is out of the path of vomit entering said interior through said inlet, and whereby vomit cannot pass out of said exhaust valve until said interior is filled to near capacity, said exhaust valve being operative to vent air upon said decrease of said volume, said exhaust valve being located on a wall of said reservoir, said collection means further including inner and outer seats and a passageway therethrough defining an exhaust opening within which said exhaust valve is received, and wherein said exhaust valve is movable between sealing and venting positions and includes an elongated body extending through said exhaust opening, said elongated body being characterized by a vent passage, said exhaust valve further including longitudinally spaced apart intermediate stop means and outer sealing means alternately engagable with said inner and outer seats in said venting and sealing positions, respectively, responsive to differential pressures across the exhaust opening, and thereby enabling egress of air from and preventing ingress of air to said interior, respectively, an elongated catheter in communication at its proximal extremity with said inlet, the distal extremity of said catheter being adapted for insertion into the throat, said catheter having an internal diameter sufficiently large to pass vomit freely toward said inlet upon said increase of said volume; and one-way inlet valve means operative upon said increase of said volume to define passage means into said catheter in the immediate region of said distal extremity to pass vomit freely through said passage means and toward said inlet and operative upon said decrease of said internal volume to close said passage means and prevent vomit in said catheter from passing back into the throat, said inlet and said passage means constituting the only openings into said catheter.

7. An aspirator according to claim 6 wherein said exhaust valve is made of elastomeric material and further includes an inner stop means, and an inner sealing means located between said inner and intermediate stop means, said inner sealing means being resiliently stretchable whereby said exhaust valve may be pulled forcibly outwardly by an operator to a discard position, reducing the cross section of said inner sealing means for location of said inner sealing means within said exhaust opening, thereby to enable said cross section of said inner sealing means to expand and seal said exhaust opening upon release of said exhaust valve by the operator.

8. An aspirator for removing vomit and like matter from the mouth and throat, said aspirator comprising:

collection means having a horizontally disposed longitudinal axis and an interior defining a proximal end and a distal end for receiving vomit and including a substantially closed reservoir having an inlet, a bellows in communication with said reservoir and having a reciprocable bellows handle oppositely movable to decrease and increase the volume of said interior, respectively, said collection means further including an inlet to said interior and a one-way exhaust valve located in the upper portion of said interior transversely displaced from said longitudinal axis and above said inlet, substantially adjacent said proximal end, whereby said exhaust valve is out of the path of vomit entering said interior through said inlet, and whereby vomit cannot pass out of said exhaust valve until said interior is filled to near capacity, said exhaust valve being operative to vent air to atmosphere upon said decrease of said volume, said interior being otherwise closed to atmosphere to prevent escape of collected vomit, said exhaust valve being located on a wall of said reservoir means;

an elongated catheter attachable at its proximal extremity to said collection means in communication with said inlet, the distal extremity being adapted for insertion into the throat, said catheter having an internal diameter sufficiently large to pass vomit freely toward said inlet upon said increase of said volume;

one-way inlet valve means operative upon said increase of said volume to define passage means into said catheter in the immediate region of said distal extremity to pass vomit freely through said passage means and toward said inlet and operative upon said decrease of said volume to close said passage means and prevent vomit in the catheter from passing back into the throat, said inlet and said passage means constituting the only openings into said catheter; and a frame adjacent said collection means and including a frame handle in opposed relation to said bellows handle to facilitate movement of said bellows handle in one direction by squeezing together said bellows handle and said frame handle, said frame including bias means engaged upon said bellows and constraining said bellows handle to move oppositely of said one direction.

* * * * *